United States Patent [19]

Mylonakis et al.

[11] 4,275,229

[45] Jun. 23, 1981

[54] POLYMERS HAVING IMPROVED WATER RESISTANCE AND MONOMERS FOR SAME

[75] Inventors: Stamatios G. Mylonakis, Barrington; Anthony J. Tortorello, Elmhurst, both of Ill.

[73] Assignee: DeSoto, Inc., Des Plaines, Ill.

[21] Appl. No.: 11,701

[22] Filed: Feb. 12, 1979

[51] Int. Cl.$^3$ .................... C07C 59/86; C07C 57/34; C08F 116/36

[52] U.S. Cl. ................... 562/459; 562/489; 562/450; 562/479; 562/595; 562/567; 260/501.1; 260/501.11; 260/501.17; 260/404; 560/82; 526/316; 526/317; 526/318; 427/13; 260/413

[58] Field of Search .................. 260/501.17, 501.1; 260/404, 260/413 562/459, 489

[56] References Cited

U.S. PATENT DOCUMENTS

| | | | |
|---|---|---|---|
| 2,874,189 | 2/1959 | Micucci et al. | 562/489 |
| 3,356,653 | 12/1967 | Sekmakas | 260/78.5 |
| 3,356,654 | 12/1967 | Sekmakas | 260/78.5 |
| 3,356,655 | 12/1967 | Sekmakas | 260/78.5 |
| 3,509,085 | 4/1970 | Sekmakas | 260/29.6 |
| 3,862,075 | 1/1975 | Sekmakas | 260/29.6 TA X |
| 3,956,374 | 5/1976 | Shepard et al. | 562/459 |
| 4,005,052 | 1/1977 | Sekmakas | 260/29.6 TA |
| 4,075,133 | 2/1978 | Sekmakas | 260/29.3 |
| 4,076,677 | 2/1978 | Sekmakas | 260/29.6 E |

OTHER PUBLICATIONS

Noller, *Chemistry of Organic Compounds,* W. B. Saunders Co., Philadelphia, pp. 795, 813–814, 1957.
Lauer et al., J.A.C.S., 75, 5406, (1953).
Sovish, Chem. Absts., 56, 2383(h), 1962.
Tahan et al., Israel J. of Chem., 11, No. 6, pp. 835–840, (1973).
Tahan et al., Chem. Absts., 82, 58420(w), (1975).
Pinazzi et al., Chem. Absts., 86, 17398(j), (1977).
Lauer et al., Chem. Absts., 49, 958(b), 1955.

*Primary Examiner*—G. T. Breitenstein
*Attorney, Agent, or Firm*—Dressler, Goldsmith, Shore, Sutker & Milnamow, Ltd.

[57] ABSTRACT

Monoethylenically unsaturated beta-carbonyl-containing carboxyl functional monomers and addition polymers containing them and other monoethylenically unsaturated monomers are disclosed, as are methods of coating substrates with the polymers to provide films of improved water resistance. The monomers are especially stable in the form of a salt with a volatile base, and the removal of the base when a polymer containing the monomer is cured causes decarboxylation, and the removal of the carboxyl groups improves the water resistance.

3 Claims, No Drawings

POLYMERS HAVING IMPROVED WATER RESISTANCE AND MONOMERS FOR SAME

DESCRIPTION

1. Technical Field

This invention relates to polymeric coating compositions and monomers useful therein.

2. Background Art

Film forming polymers useful as coating compositions frequently possess carboxylic acid moieties to assist in the solubility or dispersibility of the polymers during and before application, to improve adhesion of the polymer film on the desired substrate, and to take part in cross-linking reactions on curing subsequent to application. The presence of such carboxylic acid groups, and their hydrophilic character, often impairs film adhesion after the coating is applied or facilitates unwanted swelling and removal of the coating during washing operations, as when a wall is washed after it has been painted.

DISCLOSURE OF INVENTION

In accordance with the present invention, carboxyl functional monoethylenically unsaturated monomers of the formula

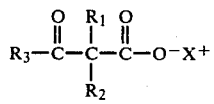

wherein $R_1$ is hydrogen or $C_1$-$C_8$ alkyl, $R_2$ is selected from hydrogen, $C_1$-$C_8$ alkyl, or a vinyl-containing radical, $R_3$ is selected from $C_1$-$C_8$ alkyl; or a vinyl containing radical; or O—$R_4$, where $R_4$ is hydrogen, $C_1$-$C_8$ alkyl or $X^+$; or $NR_5R_6$ where $R_5$ and $R_6$ are hydrogen or $C_1$-$C_8$ alkyl; and one of $R_2$ and $R_3$ is a vinyl containing radical, and $X^+$ is selected from the group consisting of the proton, protonated volatile bases, and mixtures thereof; are prepared.

One preferred structure has the following formula:

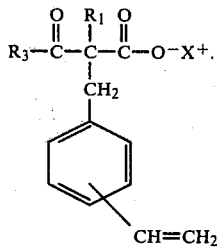

The invention includes the monomers as well as addition polymers containing these monomers and other monoethylenically unsaturated monomers. Carboxyl functional polymers of monoethylenically unsaturated monomers which are stable in the form of salts of volatile bases, but which release carbon dioxide when the base is removed are particularly contemplated.

Polymeric coatings made in accordance with this invention using the monomers disclosed herein have improved water resistance. The improved resistance to aqueous liquids is obtained by the decarboxylation of the polymerized novel monomers of this invention. The desired decarboxylation occurs slowly at ambient temperature, so air dry latex coating compositions are a feature of this invention. This decarboxylation is more rapid at elevated temperatures, such as those used for baked-on coatings. Both the monomers and polymers of this invention are more stable in alkaline medium, and decarboxylate readily under acidic conditions, so salts with volatile bases are particularly contemplated.

The novel monoethylenically unsaturated monomers of this invention contain a group or radical designated as $R_1$ in the structural formula. This radical is located at the 2- or alpha-position relative to the carboxyl group. This $R_1$ radical may include lower alkyl groups such as methyl, ethyl, sec-butyl, hexyl, or other alkyl groups containing up to 8 carbon atoms, but $R_1$ is preferably hydrogen. Hydrogen is preferred for the $R_1$ group because starting materials having two hydrogens alpha to the carboxyl functionality are commercially available and are thus inexpensive, and also because the presence of an alkyl group alpha to the carboxyl reduces the yield of the desired monoethylenically unsaturated monomer produced by the preferred method of synthesis in comparison with that obtained using hydrogen.

As shown in the preferred structural formula, the monoethylenically unsaturated monomers of this invention may owe their monoethylenic unsaturation to the vinyl benzyl group which is bonded via its methylene group to the alpha-position of the carboxyl-containing portion of the monomer. The preferred monomers of this invention and the preferred structure shown hereinbefore representing these monomers include the three possible positional isomers of the vinyl and methylene groups on the benzene ring. This is shown schematically by showing no specific positional relationship between the vinyl and methylene groups within the monomer in the above structural formula.

One of $R_2$ and $R_3$ is selected from a vinyl-containing radical. As used herein, a vinyl-containing radical is a radical or moiety which contains at least one monoethylenically unsaturated group. Thus, the vinyl benzyl group depicted in the preferred structure is one such vinyl-containing radical. Other $R_2$ and $R_3$ vinyl-containing radicals include, but are not limited to allyl derivatives such as the allyl group itself, allyl alcohol and allyl amines, such as N-methyl allylamine. Thus, $R_3$ may be derived from N-methyl allylamine to give a half N-methyl allylamide. Similarly, $R_2$ may be the allyl group itself to yield an alpha-allyl substituted monomer such as 2-allylacetoacetic acid, where $R_3$ is methyl and $X^+$ is hydrogen. Additionally, the vinyl-containing radical may be ethylene or a substituted ethylene. For example, where $R_1$, $R_2$ and $X^+$ are hydrogen and $R_3$ is ethylene, the monomer would be derived from 3-oxo-4-pentenoic acid. Acrylic or methacrylic acid derivatives are still other vinyl-containing radicals contemplated by this invention. Thus, other monomers in accordance with this invention include the acrylate ester of tartronic acid (hydroxymalonic acid) where $X^+$ is hydrogen and $R_3$ is O—H.

The monomers of this invention have a carbonyl group which is linked to the remaining monomer structure at the carbon atom alpha to the carboxyl functionality, thereby making the carbonyl group beta to the carboxyl group. The carbonyl group may be joined to various $R_3$ radicals as defined hereinbefore. Thus, the $R_3$ radical may have an alkyl or vinyl-containing radical linked to the carbonyl, making the monoethylenically unsaturated monomer a beta-keto acid, such as an alpha-substituted acetoacetic acid derivative. It will be noted that the vinyl benzyl group may be one of the alpha-substituents, as described hereinbefore. Additionally, the $R_3$ radical may form part of a carboxylic acid or derivative thereof, such as a carboxylate salt, an amide or an ester, so the monomer could be considered a derivative of a beta-dicarboxylic acid, such as an alpha-substituted malonic acid. Examples of such dicarboxylic acid derivatives include the alpha-substituted malonic acids, and mono- or dicarboxylate salts of the alpha-substituted malonic acids. Additionally, half-amides of the beta-dicarboxylic acids, such as an alpha-substituted malonic acid N-methylamide, half-esters of the beta-dicarboxylic acids, such as alpha-substituted monoethyl malonate and the like are also contemplated by the present invention.

When mono- or dicarboxylate salts are used, it is preferred that the cation be a protonated form of a volatile base rather than the proton itself.

Referring more particularly to the preferred volatile bases, these bases are illustrated by monoethanolamine, diisopropylamine, dimethylethanolamine, ammonia, triethylamine, and the like. These volatile nitrogenous bases are well-known to the art and may be primary, secondary or tertiary amines as desired.

Although several beta-carbonyl carboxylic acid-containing monoethylenically unsaturated monomers are contemplated by this invention, two classes, and their salts with volatile amines, are presently preferred. These two classes are the beta-keto acids and the beta-dicarboxylic acids. Of these two classes, the beta-keto acids are particularly preferred, and of the beta-keto acids those in which the $R_3$ group is methyl are most preferred.

The primary reasons for preference of the beta-keto acid and the beta-dicarboxylic acid monoethylenically unsaturated monomers, and their protonated volatile amine salts, are economic. Both of these monomer classes may be prepared from materials which are relatively inexpensive items of commerce, and their preparation is by straight-forward reactions of organic chemistry requiring relatively few steps. An example of one such preparation is given hereinafter in Example 1.

As the improved water resistance of the polymeric coatings of this invention is thought to be due to the loss of carboxyl functionality by decarboxylation during cure of the coating, the beta-keto acid containing monoethylenically unsaturated monomers are preferred over the otherwise preferred beta-dicarboxylic acids. This preference is explained by the presently understood mechanism by which decarboxylation takes place. According to this presently understood mechanism, the beta-dicarboxylic acid class leaves one hydrophilic, carboxylic acid or carboxylate group after decarboxylation while the beta-keto acids leave a more hydrophobic alkyl group. Thus, if the decarboxylation reaction proceeds as is presently believed, some water sensitivity due to the remaining carboxylic acid functionality is to be expected when the beta-dicarboxylic acid containing monomers are used. When coating polymers require carboxylic acid functionality to improve adhesion of the coatings to the coated substrate, some water sensitivity due to residual carboxyl functionality from the beta-diacids, left after cure, can be tolerated. Thus, using the beta-dicarboxylic acid monomers, the benefits of increased ease of dispersion found when two acid functionalities are present per monoethylenically unsaturated monomer unit may be reaped along with improved adhesion properties due to the residual acid functionality left after curing and decarboxylation.

However, when little or no residual acid functionality is desired in the cured polymer coating film, while some carboxylic acid functionality is needed for ease in dispersing the monomers or the resultant polymers, the beta-keto acid containing monoethylenically unsaturated monomers are particularly preferred, as these monomers decarboxylate to give off carbon dioxide and leave hydrophobic groups which are not as subject to attack by water as are residual carboxylic acids and their derivatives.

The particularly preferred beta-keto acid containing monomers are also useful for making polymers where one amount of carboxylic acid functionality is desired during polymerization or dispersion and a smaller amount is desired for purposes such as adhesion of the cured films. In these polymers, although the beta-dicarboxylic acid containing monomers of this invention may be used in whole or in part for this purpose, a less expensive monoethylenically unsaturated carboxylic acid, such as acrylic or methacrylic acid, is used in conjunction with the particularly preferred beta-keto acid derivative monomers of this invention. With such mixtures, the amount of less expensive carboxylic acid monomer used is typically the amount of residual acid functionality desired, while the amount of beta-keto acid derivative of the monomer of this invention used, is that amount which together with the amount of less expensive acid monomer gives the desired dispersion or solubility to the polymer.

The amount of the monomers of this invention which are used in polymers can vary greatly. Based on the free acid weight, these monomers are used at about 1 to about 60 percent by weight of the total monomers present, with the preferred amounts being about 1 to about 20 percent of the total monomers present. The specific amount selected will vary with the desired polymer characteristic as is well known.

The polymers prepared in accordance with this invention may be prepared in aqueous emulsion, aqueous dispersion, or in solvent solution. Although the free acid form of the monomers of this invention may be used during polymerization, it is preferred that the monomers be present during and after polymerization as salts with volatile amines. This is because the polymerizations are carried out at elevated temperature, and unless the carboxyl functional monomer is in its salt form, it may decarboxylate, thereby prematurely losing the desired carboxyl functionality. For example, it has been found that the presently preferred acid monomer prepared in Example 1 (used as the volatile amine salt of alpha-methylene vinyl benzyl, beta-keto acetoacetic acid) decarboxylates at about 100° C. to give carbon dioxide and the methyl-terminated monoethylenically unsaturated ketone. Of course, should the polymerization be carried out at a temperature below which decarboxylation of the free carboxylic acid form of the monomer does not occur to a significant extent (i.e., less than about 5 percent), the monomer need not be neutralized prior to polymerization. Thus, while it is not preferred, the monomer need not be preneutralized, but may also be prepared and used in its acid form or prepared as an acid and neutralized at some later time.

Neutralization of the monoethylenically unsaturated monomers may be done by means well-known in the art. Thus, the monomers may be initially prepared as salts of the bases or the salts may be prepared after the monomer is dissolved or dispersed in the polymerization medium.

The polymers of this invention may be prepared by typical addition polymerization techniques in that the monomers of this invention polymerize in a fashion similar to vinyl toluene derivatives. In addition, because of their hydrophylic nature, water soluble addition polymers may also be prepared.

U.S. Pat. Nos. 3,862,075 and 4,005,052, both to K. Sekmakas, relate to copolymers whose monomers are comprised of about 1 to 30 percent of monoethylenically unsaturated carboxylic acid functional monomers, which are polymerized in the presence of a polyhydric alcohol and which may be cured in the presence of a polyhydric alcohol and which may be cured in the presence of aminoplast resins. In these patents, the carboxylic acid functionality serves in part to aid the stability of the dispersions which are formed both during polymerization and thereafter. Additionally, the acidic copolymers are partially neutralized with volatile bases to again, in part, assist the stability of the system. On curing, the aminoplast resin may react both with the alcohol functionality present as well as with the carboxylic acid functionality present to crosslink or cure the coating composition. However, not all of the acid functionality is consumed on crosslinking, thereby leaving some unreacted acid which can cause undesirable properties when the cured coatings are later exposed to water or aqueous liquid. By substituting the monomers of the present invention for part of the monoethylenically unsaturated carboxylic acid functional monomers described in these patents, the coatings resulting after cure become less sensitive to water, presumably due to the above described decarboxylation which is speeded by heat curing.

Polymers containing carboxylic acid groups are also frequently used for electrodepositing coatings from an aqueous bath at the anode. In such systems, the carboxylic acid moiety, or more properly the carboxylate moiety, is used principally to provide a negative electrical charge to the water-dispersed polymer so that the polymer will be deposited from the dispersion onto the positively charged anode to form a coating thereon. Such electrodeposition compositions usually contain less than about 20 percent of resin solids and are frequently cured with heat while in admixture with aminoplast resins. Examples of such systems may be found in U.S. Pat. Nos. 4,075,133 to K. Sekmakas and R. Shah and 4,076,667 to K. Sekmakas. Replacement of some or all of the monoethylenically unsaturated carboxylic acid monomer used in these patents, with the monomers of the present invention achieves a similarly negatively charged water-dispersible copolymer which electrodeposits at the anode, but the modified copolymer shows improved resistance to corrosion and chemical attack after curing.

U.S. Pat. Nos. 3,356,653, 3,356,654, 3,356,655 and 3,509,085 to K. Sekmakas disclose aqueous copolymers particularly adapted to form adherent air dry latex coatings (house paints), and these may include up to about 5 percent by weight of unsaturated carboxylic acids, usually about 0.2-2 percent thereof. These acids can be replaced in whole or in part by the carboxylic acid salts of this invention to provide paints which dry to superior scrub resistance. In this regard it is stressed that the redox copolymerization of monoethylenically unsaturated acids in aqueous emulsion is normally carried out in the presence of a volatile base to provide a pH above 7, so if the acids salt were not formed in the monomer emulsion, it would be formed during the copolymerization.

Thus, it is a feature of the present invention to provide monoethylenically unsaturated monomers which are stable in the form of salts with volatile bases but which decompose by releasing carbon dioxide ($CO_2$) when the base is removed by volatilization. These polymers release $CO_2$ slowly at ambient temperature after the volatile base has evaporated, which functions to decrease the pH until the presence of the carboxyl groups provides a neutral to acidic medium, (but in any event a less stable environment for the monomers of this invention). The removal of the volatile base and the decarboxylation to release $CO_2$ is also a function of temperature and it proceeds more rapidly at elevated temperatures, such as are typically encountered during heat curing. These polymers are addition copolymers comprised of monoethylenically unsaturated monomers, such as styrene, acrylonitrile, methyl methacrylate, butyl acrylate, vinyl acetate, and like nonreactive monomers, and the monoethylenically unsaturated monomers of this invention which release $CO_2$ in acidic medium with the rate of release being a function of temperature.

BEST MODES FOR CARRYING OUT THE INVENTION

EXAMPLE 1

Preparation of Novel Monomer

Pieces of metallic sodium (2.3 g, 100 mm) are added with agitation to a reactor containing 100 ml of absolute ethanol at a rate to prevent boiling of the ethanol. The resulting solution is then cooled externally to about ambient temperature. Ethyl acetoacetate (13.01 g, 100 mm) is then added with continuous agitation. Vinyl benzylchloride (15.25 g, 100 mm) is then added dropwise and the resulting reaction mixture allowed to react at room temperature overnight.

The resulting monoethylenically unsaturated beta-keto acid ester is recovered by first evaporating the reaction mixture to a point at which it contains about 80 percent solids. The concentrated solution is then extracted with diethyl ether, the ether extract washed with water containing 10 percent by volume of concentrated hydrochloric acid, dried over magnesium sulfate, and filtered. The ether portion of the filtered extract is then evaporated under reduced pressure at or below about 23° C. to give a 90% yield of the monoethylenically unsaturated beta-keto ester which is a liquid at room temperature.

Care must be taken at this stage in the synthesis lest the monomeric beta-keto ester polymerize. Thus, a polymerization inhibitor, such as phenothiazine, is added prior to evaporation of the ether.

The monoethylenically unsaturated beta-keto ester is then placed in a 5% by weight aqueous sodium hydroxide solution of sufficient volume to have a 0.5 molar excess of hydroxide ion over the moles of monoethylenically unsaturated beta-keto ester. This solution is stirred overnight at room temperature. Concentrated hydrochloric acid is then added dropwise with cooling until the solution pH is about 3. The resulting solution of monoethylenically unsaturated beta-keto acid is then extracted with diethyl ether, dried and filtered as described above to yield an etherial solution of the acid monomer. Evaporation of the ether results in a 10% yield of the new beta-keto acid monomer of this invention which decarboxylates at about 100° C.

EXAMPLE 2

Heat Curable Copolymer Electrocoating Composition

| Charge (Grams) | Composition |
| --- | --- |
| 125 | Butanol |
| 250 | Deionized water |
| 2.5 | Benzoyl peroxide |
| 10 | An ionic surfactant (Note 1) |
| | Charge to reactor and heat to 75° C. with agitation. |
| 27 | Triol (Note 2) |
| 150 | Iso-butyl acrylate |
| 215 | Ethyl acrylate |
| 100 | Hydroxyethyl acrylate |
| 10 | Acrylic acid |
| 50 | Monoethylenically unsaturated acid monomer of Example I |
| 2.5 | Benzoyl peroxide |

Premix triol and monomers to provide a liquid mixture and add with agitation to reactor over a 3 hour period at 75° C. to 77° C. Hold for 1 hour.

| | | |
| --- | --- | --- |
| 1.5 | Tertiary-butyl perbenzoate | |
| | Add catalyst and hold for one hour at 77° C. | |
| 200 | Deionized water | |
| 37 | Diisopropanolamine | |
| | Cool to 35° C. and add water and amine. | |
| 155 | Deionized water | |
| | Add water. | |

Note 1: An anionic surfactant such as that known under the trade name Sipex DS-10, a product of Alcolac, Inc. may be used.

Note 2: A propylene oxide adduct of trimethylol propane having an average molecular weight of about 2540.

The product is a partially neutralized milky dispersion and is directly useful for maintaining the solids content of the electrocoating bath at a desired solids content, e.g., 9% by weight. The dispersion is fully neutralized by the excess amine present in the electrocoating bath. In the initial charge to the electrocoating bath, the product is diluted and fully neutralized with diisopropanolamine. The electrocoating bath includes 25%, based on the total weight of polymer, of American Cyanamid XM 1116, which is a methylated, ethylated, hexamethylol melamine. The carboxyl functionality present in the electrocoated film due to the novel monomer of this invention is lost by decarboxylation during the heat cure of the resin film, thereby improving the resistance of the film to later attack by water.

EXAMPLE 3

Low Temperature Curing Ester Copolymers-Phenolic Condensates

| Charge (Grams) | Composition |
| --- | --- |
| 820 | Diglycidyl ether of bisphenol A having an epoxide equivalent weight of 900 |
| 310 | Conjugated 9-11 castor fatty acids |
| 310 | Tall oil fatty acids |
| | Set Dean Stark trap with xylol. Heat to 150° C. to melt. Then add the following: |
| 60 | Xylol |
| 3 | Triethylamine |
| | Heat to 225° C. and hold for an acid value of 15–17. |
| | Cool to 125° C. and add the following solvents: |
| 1200 | 2-Butoxyethanol |
| | Premix the following monomers and catalysts and add over 3 hours at 120°–125° C. |
| 900 | Styrene |
| 40 | Acrylic acid |
| 300 | Monomer of Example 1 |
| 60 | Hydroxyethyl acrylate |
| 200 | Triethylamine |
| 15 | Ditertiary-butyl peroxide |
| 45 | Cumene hydroperoxide |
| 20 | Tertiary-butyl mercaptan |
| 350 | 2-butoxyethanol |
| | Hold for one hour at 120° C. |
| 10 | Cumene hydroperoxide- add and hold for 1 hour. |
| 10 | Cumene hydroperoxide- add and hold for 2 hours. |
| | Add the following solvent and phenolic resin: |
| 560 | 2-Butoxyethanol |
| 640 | Phenolic resin (Note 1) |
| | Hold for 2 hours at 120° C. for condensation. |

Note 1: The phenolic resin is provided by heat reacting para-tertiary-butylphenol with formaldehyde in water containing a small portion of methanol (provided by using 37% Formalin). The formaldehyde to phenol mole ratio is 1:1 and the reaction is carried out at 60% solids in the presence of an acid catalyst (paratoluene sulfonic acid at 0.15% based on the phenol). The reaction is carried out at 200° F. for 3 hours to produce a water dispersion. The product is diluted with 2-butoxyethanol and the water is removed to provide a solution of 60% solids content in 2-butoxyethanol. The commercial product CAM 2400 supplied by Union Carbide Corporation is preferred.

The solution product is dispersed in water by adding sufficient dimethylethanolamine to neutralize 100% of the acidity. Water solutions are prepared at 40% solids and coated on zinc phosphate treated steel panels. The coated panels are baked at 275° F. to provide hard and flexible coatings. These panels show improved condition on immersion in water as well as exposure to a 5% salt spray solution.

EXAMPLE 4

Aqueous Polymerization Of Unsaturated Monomers Using Trihydric Alcohols To Produce Emulsifier-Free Dispersions

| Charge (Grams) | Compositions |
| --- | --- |
| 500 | Deionized water |
| 0.75 | Ammonium persulfate |
| | Charge into reactor and heat to 90° C. Then prepare a monomer premix consisting of the following: |
| 170 | Styrene |
| 10 | Acrylic acid |
| 150 | Acidic monomer of Example I |
| 155 | Ethyl acrylate |
| 8 | Polyhydric alcohol (Note 1) |
| 83 | Triethylamine |
| 14 | Tertiary-dodecyl mercaptan |

| Charge (Grams) | Compositions |
|---|---|
| | Prepare a catalyst premix consisting of: |
| 375 | Deionized water |
| 3 | Ammonium persulfate |
| | Add the monomer premix and the catalyst premix solution to the reactor, simultaneously, over a 2½ hour period at 85–90° C. using fast speed agitation. When addition is complete, hold the temperature at 85° C. for an additional 90 minutes. Cool to 30° C. and neutralize with the following solution: |
| 36 | Dimethylethanolamine |
| 185 | Deionized water |

Note 1: A liquid trihydric polyoxypropylene derivative of trimethylol propane having an average molecular weight of 2540, an hydroxyl number (KOH/g) of 63, and a viscosity at 25° C. of 440 centipoise.

The dispersion of Example 4 is blended with a water soluble hexamethoxymethyl melamine resin to provide a ratio of dispersion solids to hexamethoxymethyl melamine resin solids of 80:20. The coating composition so provided is then applied to aluminum panels using a wound-wire rod to deposit the wet coating having a thickness of about 0.5 mil. The coated panels are baked in an electric oven at 475° F. for 60 seconds to cure. The cured panels have hard coatings, show no discoloration and are resistant to both methyl ethyl ketone saturated cloth rubbing (30 double rubs) and contact with water.

EXAMPLE 5

Aqueous Emulsion Copolymerization 1,620 grams of water, 3 grams of sodium bicarbonate and 9 grams of potassium persulfate are heated in a reactor under a nitrogen blanket to 170° F. A monomer emulsion is then provided by dissolving 24 grams of sodium lauryl sulfate and 72 grams of nonylphenol adducted with 20 moles of ethylene oxide per mole of the phenol in 1,600 grams of water. 131 grams of the unsaturated hydroxy amine of Example 1 of U.S. Pat. No. 3,356,655 is then mixed into this solution. A mixture of monomers is then prepared by mixing 1,920 grams of ethyl acrylate, 930 grams of methyl methacrylate, 15 grams of glycidyl methacrylate and 30 grams of acidic monomer of Example 1. This monomer mixture is added to the surfactant solution with high speed agitation to provide the monomer emulsion which is added to the reactor over 2½ hours while maintaining 170° F. to 175° F. The emulsion product is cooled to 90° F. and 75 grams of ammonium hydroxide are added to adjust the pH to about 9.5.

The product can be pigmented with titanium dioxide to provide house paints adapted to provide superior exterior durability.

I claim:

1. Carboxyl functional monoethylenically unsaturated monomer having the formula:

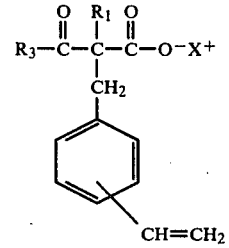

wherein $R_1$ is selected from the group consisting of hydrogen and $C_1$–$C_8$ alkyl;

$R_3$ is selected from the group consisting of $C_1$–$C_8$ alkyl, $O$–$R_4$ where $R_4$ is hydrogen or $X^+$; and $X^+$ is selected from the group consisting of the proton, protonated volatile bases, and mixtures thereof.

2. The monomer of claim 1 wherein $R_3$ is methyl, $R_1$ is hydrogen and $X^+$ is a protonated volatile amine.

3. Carboxyl functional monoethylenically unsaturated monomer having the formula:

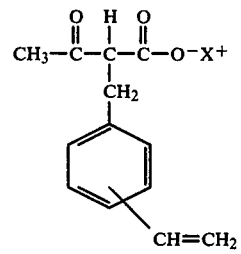

wherein $x^+$ is selected from the group consisting of the proton and protonated volatile amines.

* * * * *